(12) United States Patent
Gutierrez-Wing et al.

(10) Patent No.: US 8,962,812 B2
(45) Date of Patent: Feb. 24, 2015

(54) METHODS OF EXTRACTING CHEMICAL COMPOUNDS FROM ORGANISMS WITH RESISTANT CELL WALLS

(71) Applicant: Board of Supervisors of Louisiana State University and Agricultural and Mechanical College, Baton Rouge, LA (US)

(72) Inventors: Maria Teresa Gutierrez-Wing, Baton Rouge, LA (US); Kelly Ann Rusch, Baton Rouge, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 0 days.

(21) Appl. No.: 13/655,925

(22) Filed: Oct. 19, 2012

(65) Prior Publication Data

US 2013/0116414 A1    May 9, 2013

Related U.S. Application Data

(60) Provisional application No. 61/557,472, filed on Nov. 9, 2011.

(51) Int. Cl.
  *A23J 1/00*  (2006.01)
  *C07K 1/00*  (2006.01)
  *C07K 14/00* (2006.01)
  *C07K 16/00* (2006.01)
  *C07K 17/00* (2006.01)
  *C07H 1/08*  (2006.01)
  *C07K 1/14*  (2006.01)
  *B82Y 5/00*  (2011.01)

(52) U.S. Cl.
  CPC ........ *C07H 1/08* (2013.01); *C07K 1/145* (2013.01); *B82Y 5/00* (2013.01)
  USPC ........................................................ 530/412

(58) Field of Classification Search
  None
  See application file for complete search history.

(56) References Cited

U.S. PATENT DOCUMENTS

2008/0155888 A1* 7/2008 Vick et al. .................. 44/308

OTHER PUBLICATIONS

Lee et al. (bioresource Technology vol. 101,pp. 575-577 , 2001).*
Xu et al. (bioresource Technology vol. 102,pp. 10047-10051 Available on line Aug. 16, 2011).*
Lengke et al. ( Langmuir , vol. 23, pp. 2694-2699, 2007).*

* cited by examiner

*Primary Examiner* — Gary Nickol
*Assistant Examiner* — Khatol Shahnan Shah
(74) *Attorney, Agent, or Firm* — Jason P. Mueller; Adams and Reese LLP

(57) ABSTRACT

A method is provided for extraction of chemical compounds from an organism having a cell wall that includes adding nanomaterials, which may be metallic nanofibers such as silver nanofibers, to the organism.

8 Claims, 1 Drawing Sheet

|  |  | Nanoparticle Concentration (ppm) & Lipid Content (%) | | | | |
| --- | --- | --- | --- | --- | --- | --- |
| T/°C | time/min | 1000ppm | 500ppm | 200ppm | 50ppm | 0ppm |
| 70 | 2 | 22.9±3.89 | 13.94±0.56 | 12.11±0.79 | 10.26±0.27 | 9.68±0.24 |
|  | 5 | 24.43±3.60 | 21.41±2.89 | 19.75±2.48 | 17.26±0.77 | 15.62±2.50 |
|  | 10 | 20.57±0.78 | 13.64±1.56 | 12.52±2.19 | 12.25±1.88 | 11.40±3.13 |
| 90 | 2 | 18.61±1.07 | 15.92±2.22 | 14.15±1.21 | 13.27±1.59 | 12.46±1.02 |
|  | 5 | 21.28±0.40 | 15.75±2.34 | 14.61±1.66 | 12.60±0.51 | 12.90±0.64 |
|  | 10 | 20.34±3.64 | 15.95±1.52 | 14.60±1.85 | 13.39±0.78 | 13.81±0.46 |

METHODS OF EXTRACTING CHEMICAL COMPOUNDS FROM ORGANISMS WITH RESISTANT CELL WALLS

CROSS-REFERENCE TO RELATED APPLICATIONS

This application claims benefit of U.S. Provisional Application 61/557,472 filed Nov. 9, 2011, which is incorporated herein by reference.

STATEMENT REGARDING FEDERALLY SPONSORED RESEARCH OR DEVELOPMENT

This invention was made with government support under grant CBET-0853 483 awarded by the National Science Foundation. The government has certain rights in the invention.

FIELD

The present invention relates to methods of extracting chemical compounds from organisms with resistant cell walls, and in a particular though non-limiting embodiment, to methods of extracting lipids and pigments from a microalgae biomass by rupturing cell walls with metallic nanofibers.

BACKGROUND

Microalgae have been promoted as one of the most ideal candidates for biofuel production. Although energy can be obtained from the microalgal biomass directly by pyrolysis or other methods, the production of liquid fuels is by far the most sought after form of energy. Lipids are the most energy-dense compounds for liquid fuel production. However, lipids must be extracted from the microalgae before the lipids may be used for fuel.

The most common methods for lipid extraction from microalgal biomass use solvents and are adapted from the procedures used for other sources, including oil seeds. Lipid extraction often requires large amounts of solvent, high temperatures, pressure and/or agitation due to cell walls of microalgae which significantly limit contact between the lipid and the solvent. Solvent extraction is limited by the extent to which the cell wall of the microorganism can be penetrated. If solvents cannot reach the lipids inside the cell, they cannot extract them. There are various methods to disrupt or rupture cell walls, including molecular methods, enzymes, detergents, and mechanical methods, which require several cleaning steps to remove the chemicals used. Heat may be applied to microalgae for some extractions, but some target chemical compounds may not be not heat stable. High temperatures used over long extraction times may lead to unwanted oxidation of fatty acids.

There are two main strategies used for solvent extraction: (1) reflux of heated solvents through the biomass, and (2) the immersion of the biomass in solvents in various proportions. The Soxhlet method, which uses solvent reflux, can be efficient for dry biomass, but requires extensive preparation of the biomass for extraction. Researchers have found that enzymatic degradation of lipids (lipolysis, oxidation) can occur before and during extraction of lipids from microalgal and cyanobacterial biomass, particularly if water is present. The Bligh-Dyer and the Folch methods are used mainly for wet biomass and are based on solvent immersion.

While these are established methods, there are numerous issues with their implementation for microalgal lipid extraction. For example, the selection of the solvent for these methods can impact the final recovery of the lipids. Further, large volumes of solvent are needed for an efficient extraction of the lipids creating a potential environmental issue.

Chloroform and hexane are commonly used for solvent extraction. With these solvents, a sequence of extractions may be needed to obtain a large percentage of the lipids. As an example, it has been determined that a two-step extraction with acetone and a five-step separation with a water-alcohol-hexane system was needed to extract 80-90% of the non-polar lipids from the biomass of a species of *Scenedesmus*. Extraction efficiencies below 50% have been reported in algal species with thick cell walls.

Solvents are used not only for lipid extraction, but also for pigment extraction. The most common solvents for this application are methanol, ethanol, dimethylformamide (DMF), acetone, and hexane. The solvent extraction of photosynthetic pigments, as in the case of lipids, requires an efficient contact of the solvents with a pigment source. Also, pigment-degrading enzymes such as chlorophyllases, which maintain activity after harvesting, can rapidly decrease the chlorophyll content of a biomass in the time between harvesting and extraction.

Extraction methods may also be employed to extract proteins from organisms with resistant cell walls. Current methods include exposure grinding with glass beads, mechanical homogenization, sonication, and others, which yield mixed results. Incomplete extraction may lead to inexact estimation of protein content in a biomass. Additionally, some procedures require long treatment times that can lead to protein degradation.

An important aspect of various chemical compound extraction methods from microalgal species having thick cell walls is rupture of the cell wall to facilitate release of the chemical compounds. Because of the issue of cell wall thickness, numerous studies have been performed to investigate pre-treatment options as a means to enhance the extraction process. These include microwave, freezing, sonication, bead beating, autoclaving, electroporation, ultrasound, high pressure homogenization and cycling, and chemical cell lysis.

The effectiveness of a cell disruption method will vary depending on the characteristics of the cells to be treated. For example, cells with a high cellulose content, and hence with more robust cell walls (i.e., *Chlorella*, and *Scenedesmus*) will be more difficult to rupture than more fragile cells like *Chlamidomonas, Spirulina*, Scytonema or Rhyzoclonium, which have low or no sporopollenin in their cell wall. It has been discovered that microwave treatment increases the lipid yield two- to threefold when compared with sonication for *Botryococcus braunii*, but autoclaving resulted in the highest efficiency for lipid extraction from *Chlorella vulgaris*, which has a more resistant cell wall.

Methods that require large inputs of energy or long pre-treatment times present challenges due to potential degradation of the target products and negative impacts on cost and energy balance. Enzymatic reactions have also been used for cell wall destruction of immobilized cells. However, the immobilization of the cells, the cost of the enzymes, and the possible effects on the lipids and pigments may be problematic in large scale use of this method.

Chemical lysis is an efficient method for cell wall rupture, but may not be suitable for sensitive products, as harsh chemicals such as strong acids or alkalis can destroy target compounds. In-situ extraction from live cells has been investigated as an alternative for cell harvesting and extraction, but it was found that the product recovery was due to the lysis of the cells and not separation of pigments and lipids from live cells, as originally hypothesized.

Other methods, such as thermochemical liquefaction, microwave-assisted extraction, and supercritical fluid extraction have gained some interest as alternatives to direct solvent extraction. The thermochemical liquefaction has the advantage of extracting lipids from wet biomass, reducing processing time. However, the process requires high temperatures and pressures. Microwave-aided extraction presents some advantages, as it allows a shorter extraction time and has shown good efficiency, particularly in multistep processes. Extraction of lipids with supercritical fluids, including carbon dioxide, has been performed with biomasses of different crops, with mixed results. Although this method has been tested for lipid and pigment extraction, the use of $CO_2$ as the carrier for oil extraction requires high pressures (and high reactor cost), representing a challenge for wide scale application.

The currently-used technologies for pretreatment and chemical compound extraction from microalgae and other organisms, by the various methods described, including solvent extraction, milking, and pretreatment of biomass, lack efficiency (energetic, economic and/or product quality), thus increasing the final cost of the pigments and oil.

Therefore, there is a need for extraction methods that increase efficiency and reduce environmental concerns, thereby reducing costs associated with extraction, including extraction of biofuels, pigments, proteins and other bio-products.

BRIEF DESCRIPTION OF DRAWINGS

FIG. 1 is a table showing results of a microwave extraction, according to an example embodiment of the present disclosure.

SUMMARY

In an example embodiment of the present disclosure, a method of extracting a chemical compound from an organism having a cell wall is providing, including: exposing the organism to a solution of nanomaterials; treating the organism with an extraction solvent; and extracting the chemical compound from the organism. The metallic nanomaterials may be silver nanofibers. A concentration of the silver nanofibers in the solution of nanomaterials may be approximately 1 ppm to approximately 1000 ppm. A concentration of the silver nanofibers in the solution of nanomaterials may be approximately 200 ppm to approximately 500 ppm. The organism may be exposed to the solution of silver nanofibers for approximately 2 minutes to approximately 30 minutes.

The organism may be at least one of microalgae and cyanobacteria. The method may further include exposing the organism to at least one of heat, light, microwave, ultrasound, agitation and ultra violet energy. The chemical compound may be at least one of a lipid, a pigment, a protein, a carbohydrate, and a nucleic acid.

In an example embodiment of the present disclosure, a method of increasing efficiency of a chemical compound extraction is provided, including: disrupting cell walls using nanomaterials; and extracting the chemical compound. The chemical compound is inside organisms having the cell walls. The organisms are exposed to a solution containing the nanomaterials.

The cell walls may be at least one of permeated and ruptured by the nanomaterials. The nanomaterials may be metallic nanofibers. The metallic nanofibers may be silver nanofibers. A concentration of the silver nanofibers in the solution may be approximately 1 ppm to approximately 1000 ppm. A concentration of the silver nanofibers in the solution may be approximately 200 ppm to approximately 500 ppm. The organisms may be at least one of microalgae and cyanobacteria. The method may further include adding at least one of heat, light, microwave, ultrasound, agitation and ultra violet energy to the organisms. The chemical compound may be at least one of a lipid, a pigment, a protein, a carbohydrate, and a nucleic acid.

In an example embodiment of the present disclosure, a method is providing, including: rupturing cell walls of organisms having cell walls by treating the organisms with a solution containing nanomaterials. The nanomaterials may be metallic nanofibers. The metallic nanofibers may be silver nanofibers. A concentration of the silver nanofibers in the solution may be approximately 1 ppm to approximately 1000 ppm. A concentration of the silver nanofibers in the solution may be approximately 200 ppm to approximately 500 ppm. The method may further include: adding at least one of heat, light, microwave, ultrasound, agitation and ultra violet energy to the cell walls. The method may further include: a treating time of approximately 2 to approximately 30 minutes.

DESCRIPTION

According to example embodiments of the present invention, nanostructured materials are used to affect the integrity of microalgae and other microorganism cells. Silver-based nanomaterials, in particular embodiments, have effects that go beyond those expected from the silver-ion concentrations. This effect may be due to an accumulation of silver nanomaterials on the surface of the microbial cell wall, promoting an increase of free radicals and oxidative stress that together with mechanical effects of the nanomaterials, may weaken and produce the failure of the cell wall. In certain embodiments, a concentration of energy in the nanomaterials may increase movement of the nanomaterials and may increase surface energy.

According to example embodiments of the present invention, to reduce times or temperatures needed and/or to optimize an extraction solvent, nanostructured materials are used to enhance the extraction process. In further embodiments of the present invention, nanostructured materials are used to rupture and/or permeate the cell walls of microalgae and/or cyanobacteria. This effect is produced through a concentration of energy, catalysis, mechanically rupturing the cells, or increasing the local concentration of reactive oxygen species. Nanostructured metals, in particular, create a concentration of energy due to differential absorption of energy. In example embodiments, energy is supplied in the form of heat, light, or microwaves. Absorbed energy may be transformed to heat or to vibration, both of which may aid in the rupturing of the cell wall.

In further embodiments of the present invention, metals are used as catalyzers in a thermochemical conversion of a biomass. The interaction of nanomaterials with the microorganisms causes cell walls to rupture or increases permeability. Various metallic nanomaterials, such as silver nanofibers, have high reactivity to biological materials and may be used for disinfection in applications, such as wastewater treatment, antiseptics, clothing and others. Use of nanomaterials in an extraction process, including metallic nanofibers prepared by wet chemistry methods, increase lipid extraction efficiency. A concentration of nanomaterials may vary from approximately 1 ppm to approximately 1000 ppm or more. Cell wall disruption is concentration and time dependent, with a higher extraction efficiency occurring at higher concentrations of nanomaterials up to approximately 1000 ppm and higher extraction efficiency as the duration of exposure is increased.

In example embodiments of the present invention, silver particles affect the microorganisms' cell walls through several routes, including chemical and electrical effects. Silver nanofibers, due to their high surface to volume ratio, provide a higher energy density in the particle surface and are more reactive. Therefore, silver nanofibers disrupt cell walls more efficiently than silver in other forms. An added effect of the nanometer scale of the fibers is the possibility of mechanical effects due to the penetration of the cell wall of the microorganisms. According to example embodiments, the disruptive effects of the silver nanofibers are used to enhance the extraction of lipids and other bioproducts and cellular components of microalgae and cyanobacteria.

EXAMPLE

Silver nanofibers were applied to rupture cells walls of a Louisiana algal co-culture. The effect of the concentration of the silver nanofibers and the extraction conditions on the lipid extraction efficiency was evaluated.

The cell rupture behavior by silver nanofibers was first confirmed through electron microscopy (TEM). For the efficiency experiments, microalgal biomass paste (~15% dry biomass) harvested from the Hydraulically Integrated Serial Turbidostat Algal Reactor (HISTAR) system was extracted. The addition of silver nanofibers to the biomass-solvent matrix significantly reduced the solvent volume and agitation time for the Folch's extraction method and the heating time and temperature for microwave-assisted lipid extraction.

The results show that neutral lipid content extraction increased from 15.62% at 0 ppm nanofibers to 24.43% at 1000 ppm nanofibers (70° C., 5 minutes; biomass solvent 1:10 w/v). See, FIG. 1. FIG. 1, shows lipid content percentage for extractions conducted at various nanofiber concentrations (0 ppm, 50 ppm, 200 ppm, 500 ppm, and 1000 ppm), various durations (2 min., 5 min., and 10 min.), and two different temperatures (70° C. and 90° C.). At a treatment time of 2 minutes, the increase in extraction is even higher—9.68% at 0 ppm nanofibers and 22.87% at 1000 ppm nanofibers for a 70° C. extraction.

In example embodiments of the present invention, the efficiency of extraction of bio-products, pigments, proteins, lipids, and other cell components from microorganisms is influenced by disruption of cell walls, allowing access to said compounds. In microalgae and cyanobacteria, in particular, resistant cells wall increase the energy and materials needed for efficient extraction. In further embodiments, heat may be used to increase efficiency.

According to example embodiments of the present invention, the use of nanomaterials as aids for cell wall rupture increases the efficiency of extraction and reduces the energy needed for such extraction. In further embodiments, the nanomaterials may be used alone, or in still other embodiments, in conjunction with microwave energy, ultrasound, agitation, heat, UV, or other source of energy to increase the recovery of the desired product.

In example embodiments of the present invention, nanomaterials aid in the cell wall rupture or permeability by mechanical effects or by interaction due to size-related high surface energy. In further embodiments, nanofibers used include silver fibers grown on cobalt seeds. In still further embodiments, the nanofibers are produced by wet chemistry.

According to example embodiments of the present invention, extraction of lipids and bioproducts from microalgae is used in the production of biofuels, pharmaceuticals, and nutraceuticals. In still other embodiments, the extraction methods are used for cell breakage for laboratory analysis of cell composition, including carbohydrates, lipids, and protein, and RNA, DNA, and organelles. In still further embodiments, the method is used in other applications where the cell wall of a microorganism represents a barrier.

In example embodiments of the present invention, nanomaterials, such as silver nanofibers, may be added to a protein extraction. The presence of nanomaterials leads to a higher extraction of proteins than procedures without nanomaterials.

While the embodiments of the present invention are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted.

What is claimed:
1. A method of extracting a chemical compound from an organism having a cell wall, comprising:
   a first step of exposing the cell wall of the organism to a solution of metallic nanomaterials such that the cell wall is disrupted;
   a second step of treating the organism with an extraction solvent; and
   extracting the chemical compound from the organism.
2. The method of claim 1, wherein the metallic nanomaterials are silver nanofibers.
3. The method of claim 2, wherein a concentration of the silver nanofibers in the solution of nanomaterials is approximately 1 ppm to approximately 1000 ppm.
4. The method of claim 3, wherein a concentration of the silver nanofibers in the solution of nanomaterials is approximately 200 ppm to approximately 500 ppm.
5. The method of claim 4, wherein the organism is exposed to the solution of silver nanofibers for approximately 2 minutes to approximately 30 minutes.
6. The method of claim 1, wherein the organism is at least one of microalgae and cyanobacteria.
7. The method of claim 1, further comprising: exposing the organism to at least one of heat, light, microwave, ultrasound, agitation and ultra violet energy.
8. The method of claim 1, wherein the chemical compound is at least one of a lipid, a pigment, a protein, a carbohydrate, and a nucleic acid.

* * * * *